US00PP11022P

United States Patent [19]

Bull

[11] Patent Number: Plant 11,022

[45] Date of Patent: Aug. 3, 1999

[54] NEW GUINEA IMPATIENS PLANT NAMED 'MARY'

[76] Inventor: Norbert Bull, Gaertnersiedlung 2, 24610 Goennebek, Germany

[21] Appl. No.: 08/881,083

[22] Filed: Jun. 23, 1997

[30] Foreign Application Priority Data

Oct. 20, 1996 [DE] Germany ..... IM 416

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 8,360 8/1993 Bull ..... Plt./87.6

P.P. 8,457 11/1993 Kientzler ..... Plt./87.6

P.P. 9,236 8/1995 Dehan ..... Plt./87.6

P.P. 10,300 3/1998 Cosner et al. ..... Plt./87.6

OTHER PUBLICATIONS

GTITM UPOVROM Citation for 'Mary' As Per DE PBR IM 00416, Jan. 15, 1997.

*Primary Examiner*—Howard J. Locker
*Assistant Examiner*—Kent L. Bell
*Attorney, Agent, or Firm*—Foley & Lardner

[57] ABSTRACT

A new and distinct cultivar of New Guinea Impatiens plant named 'Mary', characterized by its violet purple flower color, medium sized, round somewhat cupped flowers, medium green foliage with light red veins, compact plant habit with medium vigor, and its medium early flowering response.

1 Drawing Sheet

The present invention comprised a new and distinct cultivar of New Guinea Impatiens, referred to by the cultivar name 'Mary'.

'Mary' is a product of a planned breeding program and was originated from a hybridization made by the invnentor Norbert Bull in a controlled breeding program in Goennebek, Germany, in 1993. The female parent was a seedling designated No. 21 and the male parent was seedling designated No. 4. Both parents are proprietary cultivars used in the breeding program.

'Mary' was discovered and selected as one flowering plant within the progeny of the stated cross by the inventor in 1994 in a controlled environment in Goennebek, Germany.

The first act of vegetative or asexual reproduction of 'Mary' was accomplished when cuttings were taken from the initial selection in Autumn 1994 in a controlled environment in Goennebek, by, or under the supervision of Norbert Bull.

Horticultural examination of plants grown from cuttings of the clone initiated in Spring 1995 in Goennebek, Germany, and continuing thereafter, has demonstrated that the combination of characteristics as herein disclosed for 'Mary' are firmly fixed and are retained through successive generations of asexual reproduction.

'Mary' has not been observed under all possible environmental conditions. The phenotype may vary significantly with variations in environment such as temperature, light intensity and day length, without, however, any variation in genotype.

The following observations, measurments, and comparisons describe plants grown in Hillscheid, Federal Republic of Germany under greenhouse conditions which approximate those generally used in commercial practice.

The following traits have been repeatedly observed and are determined to be basic characteristics of 'Mary', which in combination distinguish this New Guinea Impatiens as a new and distinct cultivar:

1. Violet purple flower color.
2. Medium sized, round, somewhat cupped flowers.
3. Medium green floiage with light red veining.
4. Compact plant habit, medium vigor.
5. Medium early flower response.

6. Resistant to powdery mildew.

Of the many commercial cultivars known to the present inventor, the most similar in comparison to 'Mary' are the commercial variety 'Papeta', disclosed in U.S. Plant Pat. No. 8,457, and the commercial variety 'Elvira' (Unpatented).

In comparison to 'Papeta', 'Mary' has a somewhat more intense flower color, its leaves are a narrower elliptical shape, and its plant habit is more compact, although it grows equally vigorously.

In comparison to 'Elvira', 'Mary' has smaller flowers which are somewhat more intense in color, darker green foliage, and a more compact plant habit.

The accompanying photographic drawing shows typical flower and foliage characateristics of 'Mary', with colors being as true as possible with illustrations of this type. In this regard, the illustration may not depict the color designations and descriptions as they accurately appear in the botanical description.

In the following description color references are made to The Royal Horticultural Society Colour chart.

The color values were determined indoors from flowers taken from plants grown in Hillscheid, Federal Republic of Germany, under greenhouse conditions which approximate those generally used in commercial practice.

The description is based on plants which were planted as rooted cuttings in 10 cm pots in early March and grown to 20° C. minimum temperature.

Classification:

*Botanical.*—A hybrid of the genus Impatiens.

*Commercial.*—New Guinea Impatiens cv. 'Mary'.

PLANT

A. General appearance and form:

*Habit.*—Compact, uniform, round, self-branching, and growth is indeterminate, although weak after flowering begins.

Heigh:—12 cm.

Width:—28 cm.

*Internode length:*—30 mm.

Stem color:—Violet red.

Flowering response: 8 weeks after planting of rooted cuttings.

*Flowering season.*—Generally indeterminate, mainly from March to October, depending on light intensity.

*Propagation.*—Usually terminal tips for cuttings.

*Rooting.*—Color is R.H.S. 159 B-C; roots initiate in about 18 days at 22° C., from sticking to transplanting.

B. Foliage:

*Leaf arrangement.*—Primarily in whorls, with the leaves somewhat upward directed.

*Shape of leaf.*—Narrow elliptic slightly asymmetric, with acute base and slightly acuminate tip.

*Margin.*—slightly serrated, ciliated.

*Leaf, length.*—*About* 140 mm.

*Leaf, width.*—About 35–38 mm.

*Main color of upper surface.*—medium green, approximately R.H.S. 137B.

*Veins on upper surface, color.*—With younger leaves, the basal part of the midrib is light red to pink; with older leaves, the midrib is only light pink fading to light green toward the tip of the leaf.

*Variegation on leaf.*—Absent.

*Main color of lower surface.*—Light green, about R.H.S. 138B.

*Veins on lower surface, color.*—Dark red.

*Petiole, color.*—Light to dark red.

*Petiole, length.*—Relatively long, about 30–40 mm.

INFLORESCENCE

A. Flower:

*Flower number per node.*—About 6, in various stages of development, usually one flower per leaf.

*Form of corolla.*—Single.

*Shape.*—Nearly round, cupped.

*Average diameter.*—60 mm.

*Color (general tonality from a distance of three meters).*—Violet purple.

*Petal shape.*—Cordate (heart-shaped), overlapping, moderately lobed.

*Petal length.*—28 mm.

*Petal width.*—27–38 mm.

*Petal texture*—Smooth, slightly glossy.

*Petal aspect.*—Borne close to the surface of the foliage, not above the foliage.

*Main color of upper surface:*R.H.S. 74A.

*Color of lower surface.*—R.H.S. 74B-C.

*Eye zone.*—Small, weak, about R.H.S. 57A.

*Spur, color.*—Dark red, R.H.S. 60A.

*Spur shape and size.*—Downwardly curved, about 45–50 mm in length.

*Pedicel, length.*—About 35 mm.

*Pedicel, color.*—Dark brown-red, R.H.S. 59A.

REPRODUCTIVE ORGANS

Androecium:

*Stamens.*—Five (5) in number, fused upper surface color is mainly R.H.S. 57B-C.

*Anthers.*—Hooded, color is about R.H.S. 11 D.

*Pollen.*—Color is about R.H.S. 4 D.

Gynoecium:

*Stigma and style.*—Five (5) in number, very short, color is about R.H.S. 11D.

*Ovary.*—Five (5) celled, 3–5 mm in length, surface color is R.H.S. 137B-C.

I claim:

1. A new and distinct cultivar of New Guinea Impatiens plant named 'Mary', as illustrated and described.

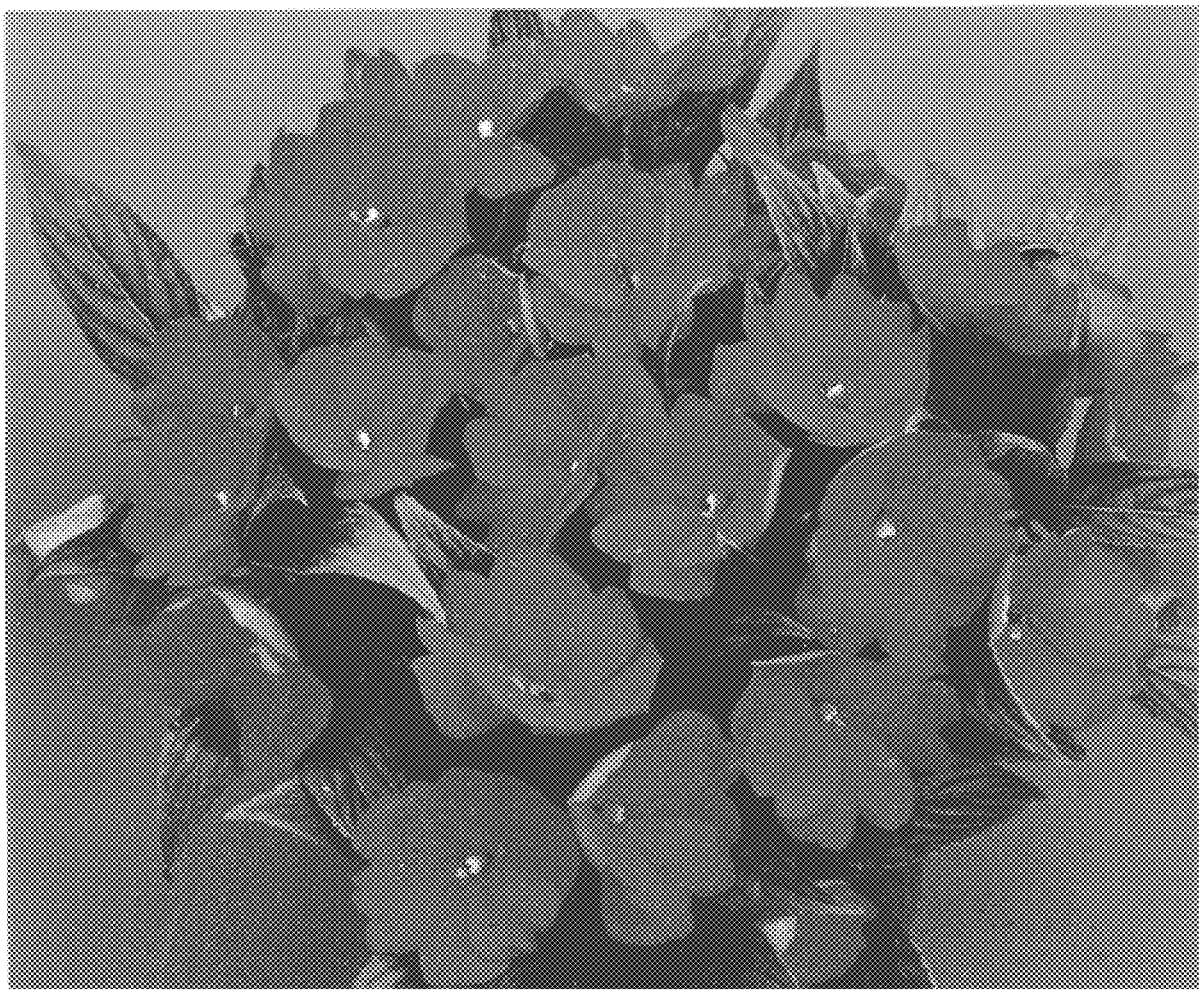

* * * * *